United States Patent [19]

Butera et al.

[11] Patent Number: 5,202,346

[45] Date of Patent: Apr. 13, 1993

[54] PIPERIDINYL AND PIPERAZINYL DERIVATIVES

[75] Inventors: John A. Butera, Kendall Park; Jehan F. Bagli; John W. Ellingboe, both of Princeton, all of N.J.

[73] Assignee: American Home Products Corporation, New York, N.Y.

[21] Appl. No.: 841,922

[22] Filed: Feb. 25, 1992

[51] Int. Cl.$^5$ .................. A61K 31/445; C07D 211/20; C07D 211/30; C07D 401/12

[52] U.S. Cl. .................................... 514/326; 514/317; 514/318; 514/327; 514/330; 514/252; 544/360; 544/366; 544/370; 544/383; 546/194; 546/210; 546/216; 546/225; 546/236; 546/240

[58] Field of Search .............. 514/317, 318, 327, 330, 514/326; 546/194, 210, 216, 225, 236, 240

[56] References Cited

U.S. PATENT DOCUMENTS

| | | | |
|---|---|---|---|
| 4,593,039 | 6/1986 | Baldwin et al. | 546/225 |
| 4,612,320 | 9/1986 | Franke et al. | 546/217 |
| 4,876,262 | 10/1989 | Oinuma et al. | 546/225 |
| 4,920,116 | 4/1990 | Morgan, Jr. et al. | 546/244 |
| 4,996,215 | 2/1991 | Oinuma et al. | 546/225 |

FOREIGN PATENT DOCUMENTS

| | | |
|---|---|---|
| 0235752 | 9/1987 | European Pat. Off. . |
| 0304888 | 3/1989 | European Pat. Off. . |
| 0320983 | 6/1989 | European Pat. Off. . |
| 9000548 | 1/1990 | World Int. Prop. O. . |

OTHER PUBLICATIONS

Bexton et al., Pharmac. Ther., 17, 315-55 (1982).
Vaughan-Williams, J. Clin. Pharmacol., 24, 129-47 (1984).
Steinberg et al., Ann. Rep. Med. Chem., 21, 95-108 (1986).
Oinuma et al., J. Med. Chem., 33, 903 (1990).
Morgan et al., J. Med. Chem., 33, 2883 (1990).

*Primary Examiner*—Cecilia Tsang
*Attorney, Agent, or Firm*—Richard K. Jackson

[57] ABSTRACT

Compounds of the formula:

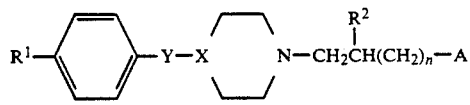

in which
$R^1$ is alkylsulfonamido of 1 to 6 carbon atoms, arylsulfonamido of 6 to 10 carbon atoms, $-NO_2$, $-CN$, 1-imidazolyl or 1,2,4-triazol-1-yl;
Y is

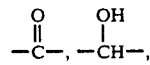

$-CH_2-$, $-O-$, $-S-$, or $-SO_2-$;
X is $-CH=$ or $-N=$;
$R^2$ is hydrogen when n is 0, otherwise it is hydrogen or $-OH$;
n is one of the integers 0, 1, 2, 3, 4, 5 or 6;
A is

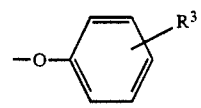

where $R^3$ is alkylsulfonamido of 1 to 6 carbons atoms, arylsulfonamido of 6 to 10 carbon atoms, $-NO_2$, $-CN$, 1-imidazolyl or 1,2,4-triazol-1-yl; or

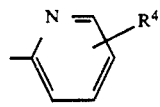

where $R^4$ is hydrogen or alkyl of 1 to 6 carbon atoms;
with the provisos that;
a) X is $-CH=$ when Y is (Abstract continued on next page.)

—O— or —S— and when Y is
and $R^2$ is —OH;
b) X is —N= when A is
c) A is
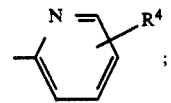
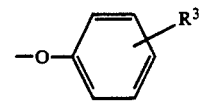
when Y is —S— or —$SO_2$— and X is —CH=, and their pharmaceutically acceptable salts are Class III antiarrhythmic agents.
8 Claims, No Drawings

PIPERIDINYL AND PIPERAZINYL DERIVATIVES

BACKGROUND OF THE INVENTION

Class III antiarrhythmic agents are recognized as having the ability to markedly prolong dog Purkinje fiber action potential duration without producing significant changes in maximal upstroke velocity. Unlike Class I antiarrhythmic agents, a pure Class III agent displays no effect on cardiac sodium channels. The electrophysiologic properties of a compound defining a Class III activity profile are observed in vivo as negligible effects on atrial, ventricular and H-V conduction times while producing a marked increase (greater than 20 percent) in both the atrial and ventricular refractory periods. In contrast, Class 1 agents demonstrate a marked slowing of ventricular conduction velocity, generally without significant changes in the refractory period. Recent reviews of these agents are: Bexton et al.; *Pharmac. Ther.* 1982, 17, 315–55; Vaughan-Williams, *J. Clin. Pharmacol,* 1984, 24, 129–47; Steinberg et al.; *Ann. Rep. Med. Chem.* 1986, 21, 95–108.

Oinuma et al. have disclosed 4'-[[1-[2-(6-methyl-2-pyridyl)ethyl]-4-piperidyl]carbonyl]methanesulfonamide (E-4031) and related piperidine derivatives as potential Class III antiarrhythmic agents in European Patent Application 0235752, Sep. 9, 1987, and further describe their pharmacology in *J. Med. Chem,* 1990, 33, 903. Closely related thio-substituted piperidines with similar activity are disclosed by Oinuma et al. in European Patent Application 0304888, Mar. 1, 1989.

Carr et al. have disclosed various 1,4-disubstituted piperidine derivatives possessing the acetamide moiety with similar Class III effects in European Patent Application 0320983, Jun. 21, 1989.

Lis et al. have disclosed derivatized alkanolamines possessing the piperazine moiety in WO 90/00548, Jan. 25, 1990 and further describe their Class III antiarrhythmic activity in *J. Med. Chem.* 1990, 33, 2883.

DESCRIPTION OF THE INVENTION

This invention provides a group of Class III antiarrhythmic agents of the formula:

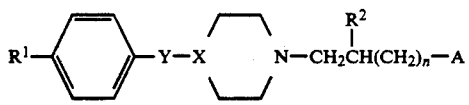

in which
$R^1$ is alkylsulfonamido of 1 to 6 carbon atoms, arylsulfonamido of 6 to 10 carbon atoms, —NO$_2$, —CN, 1-imidazolyl or 1,2,4-triazol-1-yl;
Y is

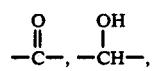

—CH$_2$—, —O—, —S—, or —SO$_2$—;
X is —CH= or —N=;
$R^2$ is hydrogen when n is 0, otherwise it is hydrogen or —OH;
n is one of the integers 0, 1, 2, 3, 4, 5 or 6;
A is

where $R^3$ is alkylsulfonamido of 1 to 6 carbon atoms, arylsulfonamido of 6 to 10 carbon atoms, —NO$_2$, —CN, 1-imidazolyl or 1,2,4-triazol-1-yl; or

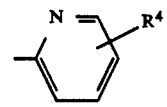

where $R^4$ is hydrogen or alkyl of 1 to 6 carbon atoms;
with the provisos that:
a) X is —CH= when Y is

—O— or —S— and when Y is

and $R^2$ is —OH;
b) X is —N= when A is

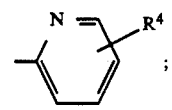

c) A is

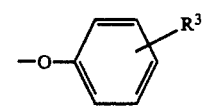

when Y is —S— or —SO$_2$— and X is —CH=,
or a pharmaceutically acceptable salt thereof.
Of these compounds, in those more preferred:
$R^1$ is alkylsulfonamido of 1 to 3 carbon atmos;
Y is

or —O—;
X is —CH= or —N=;
n is 0 or 1
$R^2$ is H when n is 0 and H or OH when n is 1;
A is

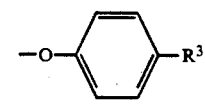

where R³ is methylsulfonamido, nitro or 1-imidazolyl, or

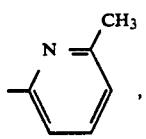

with the provisos that:
a) X is —CH= when Y is

and R² is —OH; and
b) X is —N= when A is

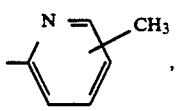

or a pharmaceutically acceptable salt thereof.
The most preferred compounds are:

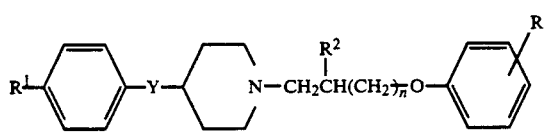

in which
R¹ is alkylsulfonamido of 1 to 3 carbon atoms;
Y is

or —O—;
R² is —H or —OH;
n is 0 or 1 and when R² is —OH, n is 1;
R³ is —NO₂, alkylsulfonamido of 1 to 3 carbon atoms or 1-imidazolyl,
or a pharmaceutically acceptable salt thereof.
In addition, the most preferred compounds include:

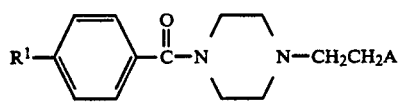

in which
R¹ is alkylsulfonamido of 1 to 3 carbon atoms;
A is

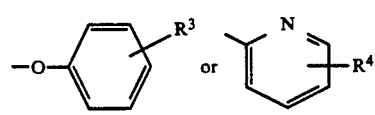

where R³ is —NO₂ or alkylsulfonamido of 1 to 3 carbon atoms and R⁴ is hydrogen or alkyl of 1 to 3 carbon atoms, or a pharmaceutically acceptable salt thereof.

The pharmaceutically acceptable salts are produced in known manner with such acids as hydrohalic, sulfuric or phosphoric acids, nitric or perchloric acid; aliphatic, alicyclic, aromatic or heterocyclic carboxylic or sulfonic acids such as formic, acetic, propionic, oxalic, succinic, glycollic, lactic, malic, tartaric, citric, ascorbic, maleic, hydroxymaleic, dihydroxymaleic, pyruvic, phenylacetic, benzoic, para-aminobenzoic, anthranilic, para-hydroxybenzoic, salicyclic, para-aminosalicyclic, methanesulfonic, ethanesulfonic, hydroxyethanesulfonic, ethylenesulfonic, toluenesulfonic, naphthalenesulfonic, sulfanilic acid, methionine, tryptophan, lysine or arginine.

Those compounds containing chiral carbon atoms, as where R² is —OH, appear as racemic mixtures which are conventionally resolved into their optical isomers. Throughout this disclosure, reference to a compound containing chiral centers is understood to embrace both the racemic mixture and each optical isomer.

The compounds of this invention in which X is —CH= and Y is —C(O)— are readily prepared by reaction of an appropriately protected 4-piperidinyl acid halide—

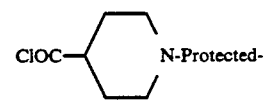

and sulfonamido benzene

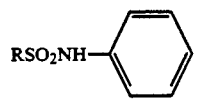

under standard Friedel-Crafts conditions (AlCl₃; CH₂Cl₂; 25°-90° C.) to obtain the 4-(4-substituted benzoyl)piperidine intermediate which is deprotected and alkylated with the desired group $$LG-CH_2CH(CH_2)_n-A$$

where LG is a leaving group, to obtain the products of this invention. Where Y is —O— or —S—, the intermediate 4-(4-substituted phenoxy(thio)) piperidine is prepared by the Mitsunobu coupling reaction of:

R¹—⟨phenyl⟩—YH with

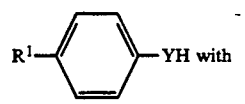

Where Y is SO₂, the thio intermediate of the product is oxidized conventionally. The piperazine derivatives (X is =N—) are prepared by coupling appropriately substituted benzoic acid—

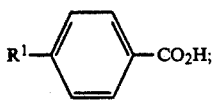

halides, alkyl esters or anhydrides with appropriately substituted piperazine derivatives—

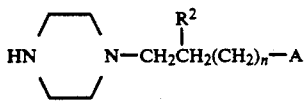

with conventional coupling agents employed in peptide chemistry. The nitro group representing $R^3$ may be reduced to an amino group conventionally (Pd/C, etc.) and acylated ($RSO_2Cl$, etc). The various reactants employed herein are either known compounds or they are routinely prepared by techniques well known in the art.

The following examples are presented to illustrate rather than limit the methods for production of representative compounds of the invention.

EXAMPLE 1

N[4-[[1-[2-(4-Nitrophenoxy)ethyl]-4-piperidinyl]carbonyl]phenyl]methanesulfonamide 4-(4-Methylsulfonylaminobenzoyl)piperidine hydrochloride (3.78 g, 11.87 mmol) was added to a stirring suspension of 1-(4-nitrophenoxy)-2-bromoethane (2.92 g, 11.87 mmol) and potassium carbonate (1.64 g, 11.87 mmol) in dimethylformamide (60 mL) and the resulting mixture was stirred at 90° C. overnight under nitrogen. The mixture was cooled and diluted with water (200 mL). A precipitate (0.93 g) was collected by filtration and triturated with diethyl ether/hexane. The filtrate was extracted with 4:1 $CH_2Cl_2$/isopropyl alcohol. The organic phase was dried ($MgSO_4$), decolorized (charcoal) and concentrated to afford a second crop of crystals (3.18 g). Combined yield: 4.11 g (77%) mp 198°-203° C.; $^1H$ NMR (DMSO-$d_6$); δ8.19 (d, J=9.31 Hz, 2H), 7.93 (d, J=8.89 Hz, 2H), 7.27 (d, J=8.83 Hz, 2H), 7.15 (d, J=9.33 Hz, 2H), 4.24 (t, J=5.72 Hz, 2H), 3.30 (m, 1H), 3.00 (m, 2H), 2.77 (m, 2H), 2.24 (m, 2H), 1.80-1.50 (m, 4H); IR (KBr): 3250, 1670 cm$^{-1}$. MS (m/z) 448 (MH+).

Elemental analysis for $C_{21}H_{25}N_3O_6S$: Calc'd: C, 56.55; H, 5.83; N, 9.46; Found: C, 56.36; H, 5.63; N, 9.39.

EXAMPLE 2

N-[4-[2-[4-[4-](Methylsulfonyl)amino]benzoyl]-1-piperidinyl]ethoxy]phenyl]methanesulfonamide The compound of Example 1 (2.00 g, 4.47 mmol) and tin (II) chloride dihydrate (8.06 g, 35.75 mmol) were stirred together in ethanol (30 mL) at 70° C. for 6 hours. The solvent was removed in vacuo and the residue was partitioned between 10% aqueous sodium bicarbonate and 4:1 dichloromethane/isopropanol. The organic phase was dried ($MgSO_4$) and concentrated to afford 1.24 g (66%) of N-[4-[[1-[2-(4-aminophenoxy)ethyl]-4-piperidinyl]carbonyl]phenyl]methanesulfonamide as a white foam which was used directly in the next step. $^1H$ NMR (CDCl$_3$); δ7.85 (d, J=6 Hz, 2H), 7.23 (d, J=6 Hz, 2H), 6.63 (m, 4H), 4.21 (br s, 2H), 4.00 (m, 2H), 3.18 (m, 3H), 3.00 (s, 3H), 2.79 (m, 2H), 2.20 (m, 2H), 1.80 (m, 4H).

To a stirring solution of the amine (1.20 g, 2.88 mmol) prepared in the preceding paragraph in dichloromethane (20 mL) at 0° C. under nitrogen was added pyridine (0.47 mL, 5.76 mmol) and methanesulfonyl chloride (0.33 mL, 4.32 mmol). The mixture was stirred at 25° C. for 2 hours and was then partitioned between 5% aqueous sodium bicarbonate and 4:1 dichloromethane/isopropanol. The organic phase was dried ($MgSO_4$), decolorized (charcoal) and concentrated to afford a residue which was triturated with ethyl acetate/diethyl ether/hexane to give the title compounds as a white solid: 0.92 g (65%). mp 168°-172° C.; $^1H$ NMR (DMSO-$d_6$): δ10.28 & 9.35 (2 s, 2H), 7.94 (d, J=8.87 Hz, 2H), 7.27 (d, J=8.85 Hz, 2H), 7.13 (d, J=9.00 Hz, 2H) 6.92 (d, J=9.01 Hz, 2H), 4.05 (t, J=5.61 Hz, 2H), 3.32 (m, 1H), 3.09 (s, 3H), 3.00 (m, 2H), 2.86 (s, 3H), 2.75 (m, 2H), 2.30 (m, 2H), 1.75-1.50 (m, 4H), IR (KBr): 3220, 1660 cm$^{-1}$; MS( m/z) 496 (MH+), 217,91.

Elemental analysis for $C_{22}H_{29}N_3O_6S_2$: Calc'd: C, 53.32; H, 5.90; N, 8.48; Found: C, 52.96; H, 5.94; N, 8.63.

EXAMPLE 3

N-[4-[[1-[3-(4-Nitrophenoxy)propyl]-4-piperidinyl]carbonyl]phenyl]methanesulfonamide 4-(4-Methylsulfonylaminobenzoyl)piperidine hydrochloride (1.97 g, 6.19 mmol) and 1-(4-nitrophenoxy)-3-iodopropane (1.90 g, 6.19 mmol) were reacted by the procedure of Example 1 to afford 1.32 g (46%) of the desired product as a white solid: mp 162°-164° C.; $^1H$ NMR (DMSO-$d_6$): δ10.29 (br s, 1H), 8.19 (d, J=9.30 Hz, 2H), 7.93 (d, J=8.86 Hz, 2H), 7.26 (d, J=8.84 Hz, 2H), 7.13 (d, J=9.31 Hz, 2H), 4.15 (t, J=6.34 Hz, 2H), 3.32 (m, 1H), 3.09 (s, 3H), 2.89 (m, 2H), 2.48 (m, 2H), 2.07 (m, 2H), 1.91 (m, 2H), 1.70 (m, 2H), 1.56 (m, 2H). IR (KBr): 3620, 3210, 2950, 1660, 1600 cm$^{-1}$.

Elemental analysis for $C_{22}H_{27}N_3O_6S$: Calc'd: C, 57.25; H, 5.90; N, 9.10; Found: C, 57.78; H, 5.87; N, 8.88.

EXAMPLE 4

N-[4-[[1-[2-[4-(Methylsulfonyl)amino]phenoxy]ethyl-4-piperidinyl]oxy]phenyl]methanesulfonamide To a cooled (0° C.) mixture of NaBH$_4$ (2.15 g, 0.057 mol) and isopropanol (70 mL) was added N-acetyl-4-piperidone (8.00 g, 0.057 mol). The mixture was allowed to warm to room temperature and stirred for 16 hours. CO$_2$ was bubbled into the reaction mixture, EtOAc (120 mL) was added, and the precipitate was removed by filtration. The filtrate was concentrated to give 8.0 g (100%) of N-acetyl-4-hydroxypiperidine as a colorless oil.

To a stirred mixture of N-acetyl-4-hydroxypiperidine (7.1 g, 0.050 mol), 4-nitrophenol (7.1 g, 0.050 mmol, (PPh$_3$ (16.3 g, 0.062 mol), and THF (50 mL) was added a solution of diethyl azodicarboxylate (10.8 g, 0.062 mol) in THF (16 mL). The mixture was stirred at room temperature for 48 hours, and then concentrated. The crude mixture was purified by flash chromatography (1% MeOH/EtOAc) to give 4.5 g (30%) of N-acetyl-4-(4-nitrophenoxy)piperidine as a yellow oil: $^1H$ NMR (DMSO-$d_6$): δ8.10 (d, 2H) 7.05 (d, 2H), 4.80 (m, 1H) 3.80 (m, 1H), 3.65 (m, 1H), 3.15 (m, 1H), 3.00 (m, 1H), 2.00 (s, 3H), 1.90 (m, 2H), 1.65 (m, 1H), 1.50 (m, 1H).

A mixture of N-acetyl-4-(4-nitrophenoxy)piperidine (1.6 g 6.05 mmol) and 2N HCL (25 mL) was heated under reflux for 3 hours. The mixture was cooled and concentrated to give 1.5 g (100%) of 4-(4-nitrophenoxy)piperidine hydrochloride as an off-white solid; mp 216°-219° C.; ¹H NMR (DMSO-d₆): δ9.05 (br s, 2H), 8.10 (d, 2H), 7.10 (d, 2H), 4.82 (m, 1H), 3.80 (m, 2H), 3.00 (m, 2H), 2.05 (m, 2H), 1.85 (m, 2H).

A mixture of 4-(4-nitrophenoxy)piperidine hydrochloride (1.15 g, 5.80 mmol), 1-bromo-2-(4-nitrophenoxy)ethane (1.43 g, 5.80 mmol), K₂CO₃ (1.60 g, 11.80 mmol), and DMF (15 mL) was heated at 90° C. for 6 hours. The mixture was cooled, diluted with CH₂Cl₂, and washed with water. The organic phase was dried (MgSO₄) and concentrated to give 1.70 g (80%) of N-2-(4-nitrophenoxy)ethyl-4-(4-nitrophenoxy)piperidine as a yellow solid. ¹H NMR (DMSO-d₆): δ8.10 (m, 4H), 7.05 (d, 4H), 4.60 (m, 1H), 4.15 (t, 2H), 2.78 (m, 4H), 2.40 (t, 2H), 1.95 (m, 2H), 1.65 (m, 2H).

N-2-(4-Nitrophenoxy)ethyl-4-(4-nitrophenoxy)-piperidine (1.50 g, 3.87 mmol) was hydrogenated in THF/MeOH (1:1, 60 mL) at 50 psi over 10% Pd/C (0.5 g) for 16 hours. The mixture was filtered through solka floc and the filtrate was concentrated. Purification by flash chromatography (8% MeOH/CHCl₃) gave 0.97 g (80%) of N-2-(4-aminopheoxy)ethyl-4-(4-aminophenoxy)piperidine as a yellow oil. ¹H NMR (DMSO-d₆): δ6.65 (d, 4H), 6.50 (d, 4H), 4.60 (br s, 4H), 4.05 (m, 1H), 3.90 (t, 2H), 2.78 (m, 2H), 2.60 (t, 2H), 2.15 (m, 2H), 1.85 (m, 2H), 1.55 (m, 2H).

To a cooled (0° C.) mixture of N-2-(4-aminophenoxy)ethyl-4-(4-aminophenoxy)-piperidine (0.97 g, 3.00 mmol), pyridine (0.50 g, 6.30 mmol;), and CH₂Cl₂ (25 mL) was added methanesulfonyl chloride (0.72 g, 6.3 mmol). The mixture was stirred at room temperature. After 4 days, the reaction mixture was taken up in 4:1 CH₂Cl₂/isopropanol and saturated aqueous NaHCO₃. The layers were separated and the organic phase was dried (MgSO₄), treated with charcoal, and concentrated to give a yellow solid. Trituration with 5% MeOH/CHCl₃ and then EtOAc gave 0.75 g (52%) of the title compound as a white solid, mp 179°-181° C. ¹H NMR (DMSO-d₆): δ9.40 (s, 2H), 7.05 (m, 4H), 6.90 (d, 4H), 4.35 (m, 1H), 4.05 (t, 2H), 2.90 (s, 6H), 3.75 (m, 4H), 2.35 (m, 2H), 1.95 (m, 2h), 1.65 (m, 2H).

Elemental analysis for C₂₁H₂₉N₃O₆S₂: Calc'd:. C, 52.16; H, 6.04; N, 8.69; Found: C, 52.23; H, 6.02; N, 8.31.

EXAMPLE 5

N-[4-[[4-[2-(4-Nitrophenoxy)ethyl]-1-piperazinyl]carbonyl]phenyl]methanesulfonamide To a stirring solution of N-acetylpiperazine (5.10 g, 40.0 mmol) in acetonitrile (100 mL) was added 1-(4-nitrophenoxy)-2-bromoethane (10.0 g, 40.0 mmol), K₂CO₃ (15 g, 108 mmol), and NaI (0.90 g, 6.0 mmol). The mixture was stirred under nitrogen at 70° C. for 24 hours, cooled, and concentrated. The residue was partitioned between ethyl acetate/10% aqueous K₂CO₃. The organic phase was dried and concentrated to afford crude product which was purified by flash column chromatography (5% CH₃OH/CH₂Cl₂) to afford 7.07 g (61%) of 1-acetyl-4-[2-(4-nitrophenoxy)ethyl]piperazine as a semisolid: ¹H NMR (CDCl₃): δ8.20 (d, J=9.6 Hz, 2H), 6.95 (d, J=9.6 Hz, 2h), 4.20 (t, J=6.0 Hz, 2H), 3.65 (m, 2H), 3.50 (m, 2H), 2.85 (t, J=6.0 Hz, 2H), 2.55 (m, 6H), 2.08 (s, 3H).

The compound of the preceding paragraph (6.78 g. 23.14 mmol) was heated in 3N HCl (70 mL) for 3 hours at reflux. The mixture was cooled, made basic with NaOH pellets to pH=10, and extracted with ethyl acetate. The organic phase was dried and concentrated to afford 5.49 g (94%) of 1-[2-(4-nitrophenoxy)ethyl]piperazine which was used directly in the next step: ¹H NMR (CDCl₃): δ8.20 (d, J=9.6 Hz, 2H), 6.95 (d, J=9.6 Hz, 2H), 4.20 (t, J=6.0 Hz, 2H), 3.00-2.45 (m, 10H).

4-(Methylsulfonylamino)benzoic acid (*J. Med. Chem.*, 1987, 30, 755; 2.02 g, 9.39 mmol) was added to a stirring solution of 1-hydroxybenzotriazole hydrate (1.27 g, 9.39 mmol) and dicyclohexylcarbodiimide (1.96 g, 9.39 mmol) in DMF (30 mL) at 25° C. under nitrogen. After 1 hours, 1-[2-(4-nitrophenoxy)ethyl]piperazine (2.59 g, 10.33 mmol) was added. The mixture was stirred overnight at 25° C. and was then filtered through a pad of Celite ®. The filtrate was partitioned between 10% aqueous NaHCO₃/dichloromethane, dried, and concentrated to afford 3.14 g (75%) of product, 0.50 g of which was treated with ethanolic HCl to afford 0.32 g of the title compound as a hydrochloride salt: mp 255°-257° C. (dec); ¹H NMR (DMSO-d₆); δ10.12 (s, 1H), 8.26 (d, J=9.34 Hz, 2H), 7.45 (d, J=8.51 Hz, 2H), 7.26 (d, J=8.72 Hz, 2H), 7.21 (d, J=9.34 Hz, 2H), 4.58 (m, 2H), 3.62-3.10 (m, 10H), 3.06 (s, 3H); IR (KBr): 3420, 3020, 2460, 1630, 1610, 1590 cm⁻¹; MS(m/z) 449 (MH⁺, 8%), 279 (20), 140 (100), 124 (40).

Elemental analysis for C₂₀H₂₄N₄O₆S.HCl: Calc'd: C, 49.53; H, 5.20; N, 11.55; Found: C, 49.52; H, 5.28; H, 11.24.

EXAMPLE 6

N-[4-[[4-[2-[4-(Methylsulfonylamino)phenoxy]ethyl]-1-piperazinyl]carbonyl]phenyl]methanesulfonamide The product of Example 5 (1.70 g, 3.79 mmol) was dissolved in ethanol (25 mL) containing 5% Pd/C (0.26 g) and the Parr vessel was charged with hydrogen (50 psi) for 18 hours. The mixture was filtered through a pad of solka floc and the filtrate was concentrated to afford 1.54 g (99%) of N-[4-[[4-[2-(4-aminophenoxy)ethyl]-1-piperazinyl]carbonyl]phenyl]methanesulfonamide as an oil: ¹H NMR (CDCl₃): δ7.40 (d, J=7.8 Hz, 2H), 7.22 (d, J=7.8 Hz, 2H), 6.75 (d, J=8.4 Hz, 2H), 6.62 (d, J=8.4 Hz, 2H), 4.00 (t, 2H), 3.80-3.20 (m, 8H), 3.00 (s, 3H), 2.80 (t, 2H), 2.60 (brs, 2H).

To the above amine (1.50 g, 3.59 mmol) in CH₂Cl₂ (30 mL) at 0° C. under nitrogen was added pyridine (0.58 mL, 7.18 mmol) and methanesulfonyl chloride (0.42 mL, 5.38 mmol). After stirring for 2 hours, the mixture was partitioned between 10% aqueous NaHCO₃ and 4:1 CH₂Cl₂/isopropanol. The organic phase was dried and concentrated to afford a residue which was treated with ethanolic HCl to give 0.85 g (48%) of the title compound as a hydrochloride: mp: 170°-175° C.; ¹H NMR (DMSO-d₆): δ10.12 (s, 1H), 9.45 (s, 1H), 7.45 (d, J=8.56 Hz, 2H), 7.25 (d, J=8.59 Hz, 2H), 7.16 (d, J=8.96 Hz, 2H), 6.97 (d, J=8.97 Hz, 2H), 4.37 (m, 2H), 3.60-3.25 (m, 10H), 3.05 (s, 3H), 2.87 (s, 3H), IR (KBr): 3010, 2580, 2460, 1640, 1610 cm⁻¹; MS (m/z) 497 (MH⁺, 10%) 198 (35), 79 (100).

Elemental analysis for C₂₁H₂₈N₄O₆S₂.HCl: Calc'd: C, 47.32; H, 5.48; N, 10.51; Found: C, 47.34; H, 5.56; N, 10.44.

EXAMPLE 7

N-[4-[[1-[3-[4-(1H-Imidazol-1-yl)phenoxy]propyl]-4-piperidinyl]carbonyl]phenyl]methanesulfonamide To a stirring solution of 4-(imidazol-1-yl)phenol (20 g, 125 mmol) and NaOH (5.0 g, 125 mmol) in methanol (600 mL) was added 1-bromo-3-chloropropane (49 mL, 500 mmol). The reaction was stirred for 18 hours at 70° C. under nitrogen, concentrated, and partitioned between 1.0N NaOH/CH$_2$Cl$_2$. The organic phase was dried and concentrated to afford crude product which was purified by HPLC (5% CH$_3$OH/CH$_2$Cl$_2$) to give 6.0 g (20%) of 1-[4-(3-chloropropoxy)phenyl]-1H-imidazole as a brown solid: mp 53°–55° C., $^1$H NMR (CDCl$_3$): δ7.80 (brs, 1H), 7.30 (m, 3H), 7.20 (bs, 1H), 4.16 (t, J=6.0 Hz, 2H), 3.76 (t, J=6.0 Hz, 2H), 2.30 (m, 2H).

4-(4-Methylsulfonylaminobenzoyl)piperidine hydrochloride (2.35 g, 7.40 mmol) and 1-[4-(3-chloropropoxy)phenyl]-1-H-imidazole (1.75 g, 7.40 mmol) were reacted in the manner of Example 1 (using 0.20 g NaI as catalyst) to afford 1.20 g (34%) of an oil which was treated with ethanolic HCl to give the title compound as the dihydrochloride: mp 173°–177° C.; $^1$H NMR (DMSO-d$_6$): δ10.76 (brs, 1H), 10.71 (brs, 1H), 10.43 (s, 1H), 9.46 (s, 1H), 8.15 (s, 1H), 7.99 (d, J=8.76 Hz, 2H), 7.80 (s, 1H), 7.72 (d, J=8.9 Hz, 2H), 7.31 (d, J=8.63 Hz, 2H), 7.17 (d, J=9.04 Hz, 2H), 4.16 (t, J=6.21 Hz, 2H), 3.66 (m, 1H), 3.60–3.05 (m, 6H), 3.11 (s, 3H), 2.24 (m, 2H), 1.97 (m, 4H); IR (KBr): 3420, 3050, 1670, 1600 cm$^{-1}$; MS (m/z) 484 (MH$^+$, 20%), 161 (100).

Elemental analysis for C$_{25}$H$_{30}$N$_4$O$_4$S.2 HCl: Calc'd: C, 54.05; H, 5.81; N, 10.09; Found: C, 52.53; H, 5.90; N, 9.96.

EXAMPLE 8

N-[4-[2-Hydroxy-3-[4-4-[(methylsulfonyl)amino]benzoyl]-1-piperidinyl]propoxyl]phenyl]methanesulfonamide A stirred solution of 4-[4-methylsulfonylaminobenzoyl]piperidine hydrochloride (2.25 g, 7.06 mmol), 2-[(4-methylsulfonyamino)phenoxy)methyl]oxirane (U.S. Pat. No. 4,994,459, 1.73 g, 7.06 mmol) and K$_2$CO$_3$ (0.98 g, 7.06 mmol) in ethanol (40 mL) was heated at 90° C. for 24 hours and then at 25° C. for an additional 24 hours. The mixture was concentrated and the residue was partitioned between aqueous 10% NaHCO$_3$ and 4:1 CH$_2$Cl$_2$/isopropanol. The organic phase was dried and concentrated to afford 2.89 g (78%) of the title compound. A portion (1.60 g) was purified by HPLC (15% CH$_3$OH/EtOAc) to give 0.92 g of product as a white solid: mp 179°–183° C. (dec); $^1$H NMR (DMSO-d$_6$): δ10.20 (brs, 1H), 9.33 (brs, 1H), 7.94 (d, J=8.72 Hz, 2H), 7.26 (d, J=8.92 Hz, 2H), 7.13 (d, J=9.13 Hz, 2H), 6.91 (d, J=8.92 Hz, 2H), 4.83 (m, 1H), 3.93 (m, 2H), 3.85 (m, 1H), 3.09 (s, 3H), 2.96 (m, 2H), 2.87 (s, 3H), 2.45 (m, 2H), 2.20 (m, 2H), 1.75–1.50 (m, 4H); IR (KBr): 3420, 3300, 3250, 2910, 1675, 1610 cm$^{-1}$; MS (m/z) 526 (MH$^+$, 25%), 217 (40), 91 (100).

Elemental analysis for C$_{23}$H$_{31}$N$_3$O$_7$S$_2$: Calc'd: C, 52.55; H, 5.94; N, 7.99; Found: C, 52.61; H, 5.99; N, 7.62.

EXAMPLE 9

1-[2-(6-Methyl-2-pyridinyl)ethyl-4-[4-[(methylsulfonyl)amino]benzoyl]piperazine

To a stirring solution of N-acetylpiperazine (2.50 g, 20 mmol) in methanol (40 mL) at 0° C. under nitrogen was added 2-methyl-6-vinyl-pyridine (2.39 g, 20 mmol) and acetic acid (1.28 mL). The mixture was stirred for 24 hours at 80° C. and was then concentrated. The residue was partitioned between 10% aqueous K$_2$CO$_3$/CH$_2$Cl$_2$. The organic phase was dried and concentrated to afford 3.60 g (73%) of 1-acetyl-4-[2-(6-methyl-2-pyridyl)ethyl]piperazine as a brown solid which was used directly in the next step: $^1$H NMR (CDCl$_3$): δ7.48 (m, 1H), 7.0 (d, 1H), 3.63 (t, 2H), 3.45 (t, 2H), 2.95–2.60 (m, 4H), 2.50 (m, s, 9H), 2.08 (s, 3H).

The compound of the preceding paragraph (4.50 g, 18.22 mmol) was hydrolyzed in the manner presented in Example 5 to afford 3.00 g (80%) of 1-[2-(6-methyl-2-pyridyl)ethyl]piperazine which was used directly in the next step: $^1$H NMR (CDCl$_3$): δ7.45 (m, 1H), 7.0 (d, 1H), 4.82 (brs, 1H), 3.10–2.60 (m, 12H), 2.50 (s, 3H).

4-(methylsulfonylamino) benzoic acid (2.16 g, 10.05 mmol) was added to a stirring solution of 1-hydroxybenzotriazole hydrate (1.36 g, 10.05 mmol) and dicyclohexylcarbodiimide (2.08 g, 10.05 mmol) in DMF (30 mL) at 25° C. under nitrogen. After 45 minutes, 1-[2-(6-methyl-2-pyridyl)ethyl]piperazine (2.27 g, 11.05 mmol) was added as a suspension in DMF (15 mL). The resulting mixture was stirred at room temperature overnight. The work-up was performed as disclosed in Example 5 to give 2.94 g (73%) of the title compound which was treated with ethanolic HCl to afford 2.15 g of product as a dihydrochloride: mp 165°–167° C.; $^1$H NMR (DMSO-d$_6$): δ10.14 (s, 1H), 8.19 (m, 1H), 7.63 (m, 2H), 7.45 (d, J=8.72 Hz, 2H), 7.25 (d, J=8.71 Hz, 2H), 3.85–3.20 (m, 12H), 3.06 (s, 3H), 2.67 (s, 3H); IR (KBr): 3420, 3000, 2560, 1640 cm$^{-1}$; MS (m/z) 403 (MH$^+$, 25%) 217 (30), 91 (100).

Elemental analysis for C$_{20}$H$_{26}$N$_4$O$_3$S.2HCl: Calc'd: C, 50.53; H, 5.94; N, 11.78; Found: C, 50.25; H, 6.25; N, 11.39.

The Class III antiarrhythmic activity of the compounds of this invention was established in accordance with standard pharmaceutically accepted test procedures in representative compounds as follows:

Bundles of free-running Purkinje fibers with attached myocardium obtained from either ventricle of adult dog heart were pinned without stretching to the bottom of a 10 mL tissue chamber and continuously superfused with oxygenated Tyrode's solution at a flow rate of 5 mL/min. The composition of the Tyrode's solution was (mM): NaCl, 138; KCl, 4; CaCl, 2; MgCl$_2$, 0.5; NaHCO$_3$, 24; dextrose, 5.5. The solution was aerated with 95% O$_2$/5% CO$_2$ at 37° C. The bath temperature was maintained at 37°±0.5° C. by circulating the prewarmed superfusate through a thermostatically controlled water bath immediately prior to entering the tissue chamber.

The preparations were stimulated through bipolar Teflon-coated silver wires, bared at the tips, placed on the endocardial surface of the attached myocardium, using a digital stimulator set to deliver constant current pulses 1.5 msec in duration at cycle lengths of 300 or 1000 msec. Stimulus strength was set at approximately 2×diastolic threshold, and adjusted as required throughout the experiment. All preparations were allowed to equilibrate in the tissue chamber for at least 1 hour before measurements were begun. Subsequently, a minimum of 60 minutes were allowed for equilibration with each drug-containing superfusate before post-drug measurements were made. Impalements were made at 6 to 10 sites throughout the preparation before and after drug exposure. Offset potentials were rechecked after each impalement.

Glass microelectrodes filled with 3M KCl were coupled to high impedance negative capacitance electrometers with Ag/AgCl half-cells used as reference electrodes. The first derivative of the action potential upstroke (V$_{max}$) was obtained using an analog differentiator circuit, coupled to a peak-hold circuit that retained the recorded value of V$_{max}$ for 30 to 70 msec. Action potential and $V_{max}$ tracings were displayed on a storage oscilloscope, and photographed for later analysis. In addition, chart paper recordings of $V_{max}$ were obtained using the peak-hold device output.

Fresh stock solutions of drug were prepared for each experiment. Compounds were dissolved in distilled water at total concentrations of 1 to 10 mg/mL, and subsequently diluted to a final concentration of 3 to 10 μM in appropriate volumes of normal Tyrode's solution for evaluation.

Action potential (AP) parameters measured included: diastolic take-off potential (or activation voltage, $V_{act}$); AP overshoot ($V_{os}$); AP duration measured as the time taken to repolarize to $-20$ mV ($APD_{-20}$), $-60$ mV ($APD_{-60}$), and $-80$ mV ($APD_{-80}$); and maximal upstroke velocity ($V_{max}$). An increase in $APD_{-60}$ that occurred without a significant change in $V_{max}$ was taken, by definition, to indicate Class III antiarrhythmic activity "in vitro".

The results of this study demonstrated activity in the representative compounds as shown in Table I.

TABLE I

| | BCL = 300 | | BCL = 1000 | |
|---|---|---|---|---|
| Example | $APD_{-60}$ | $V_{max}$ | $APD_{-60}$ | $V_{max}$ |
| 1 | 25 (0.03 μM) | −7 | 42 (0.03 μM) | −1 |
| 2 | 30 (0.10 μM) | 3 | 45 (0.10 μM) | −2 |
| 3 | 47 (0.3 μM) | 6 | 98 (0.3 μM) | 35 |
| 4 | 50 (0.3 μM) | 4 | 93 (0.30 μM) | 36 |
| 5 | 28 (0.3 μM) | 10 | 52 (0.3 μM) | −3 |
| 6 | 33 (3 μM) | 1 | 52 (3 μM) | −7 |
| 8 | 11 (1 μM) | −10 | 21 (1 μM) | 4 |
| 9 | 11 (0.10 μM) | 13 | 15 (0.10 μM) | 10 |

In addition, in vivo studies with the compounds of this invention were performed in accordance with the following standard test procedure.

Mongrel dogs of both sexes weighing 12 to 18 kg were anesthetized with sodium phenobarbital (35 mg/kg i.v. supplemented with 5 mg/kg/h) and artificially ventilated with room air (minute volume: 200 mL/kg).

The heart was exposed by a right thoracotomy performed at the fifth intercostal space and suspended in a pericardial cradle. Epicardial electrodes for stimulation and recording were sutured to the free wall of the lower right atrium and near the base of the right ventricle. Each electrode set contained a linear array of electrodes consisting of 1 bipolar stimulating electrode and 2 bipolar recording electrodes embedded in a rigid acrylic matrix. The stimulating bipole was 7 mm from the proximal recording electrode, which in turn was 10 mm from the distal recording bipole. Each electrode array was oriented to be parallel to the epicardial fiber axis.

Arterial blood pressure and lead ECG were displayed on a chart recorder and monitored on an oscilloscope. Conduction times and refractory periods were measured during pacing at a cycle length of 300 msec. The dog heart was paced by a stimulator driving a constant current isolation unit. Electrical signals from the atrial and ventricular electrodes were displayed on a digital oscilloscope and recorded on an ink-jet recorder. The diastolic blood pressure (BP) and heart rate (HR) were determined before and after each trial.

Refractory periods of the right atrium and right ventricle (AERP and VERP) were determined by introducing an extrastimulus ($S_2$) every 8 paced beats ($S_1$). The extrastimulus was followed by a 4-second rest interval during which no pacing occurred. Both $S_1$ and $S_2$ were of identical intensity (twice threshold) and duration (2 msec). The $S_1$-$S_2$ interval was gradually decreased in 2 msec steps until the extrastimulus failed to induce a propagated response. This $S_1$-$S_2$ interval was considered to define the effective refractory period.

Atrial and ventricular conduction times (ACT and VCT) were measured as the time interval between the two electrograms recorded at the proximal and distal sites of the recording electrode array. The time of activation for electrograms with predominantly biphasic complexes was taken as the moment when the trace crossed the zero reference line, and for triphasic complexes, as the peak of the major deflection.

Animals received the test compound by i.v. injection. The compound was administered over a 3 minute period. Electrophysiologic testing was performed 15 minutes following the end of dosing. Every 30 minutes the dog received the next incremental dose.

Vehicle-treated animals did not show any significant change of the electrophysiologic parameters. An increase in ERP that occurred without a significant decrease of CT was taken, by definition, to indicate "in vivo" Class III antiarrhythmic activity.

The results of this in vivo study with the compounds of Examples 1, 2, and 9, representative of the other compounds of the invention are given in Table II.

TABLE II

| Example | Dose | AERP | VERP | ACT | VCT | HR | BP |
|---|---|---|---|---|---|---|---|
| 1 | 0.05 mg/kg | 26 | 28 | 4 | −6 | −20 | −4 |
| 2 | 0.20 mg/kg | 32 | 14 | 0 | 0 | −17 | −14 |
| 9 | 1.0 mg/kg | 43 | 9 | 4 | 3 | −21 | 10 |

Based upon the activity profile elicited by the compounds of this invention in the above-described standard scientifically recognized test models, the compounds are established as antiarrhythmic agents useful in the treatment of cardiac arrhythmia and fibrillatory conditions characterized by coronary artery vasospasm. For that purpose, the compounds may be administered orally or parenterally in suitable dosage forms compatible with the route of administration, whether oral, intraperitoneal, intramuscular, intravenous, intranasal, buccal, etc. The effective dose range determined in the animal test models has been established at from about 2 to about 20 milligrams per kilogram host body weight (preferably from 2 to 10 mg/kg) i.v., and from about 40 to about 100 mg/kg (preferably 40 to 50 mg/kg) p.o., to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tables, capsules, solutions, etc., which comprise a unit dose (e.g. from about 2 milligrams to about 100 milligrams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

What is claimed is:

1. A compound of the formula:

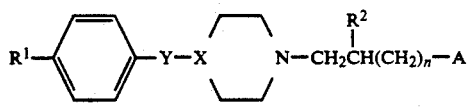

in which

R¹ is alkylsulfonamido of 1 to 6 carbon atoms, alkylsulfonamido of 6 to 10 carbon atoms, —NO₂, —CN, 1-imidazolyl or 1,2,4-triazol-1-yl;

Y is

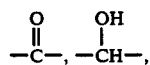

—CH₂—, —O—, —S—, or —SO₂—;

X is —CH=;

R² is hydrogen when n is 0, otherwise it is hydrogen or —OH;

n is one of the integers 0,1,2,3,4,5 or 6;

A is

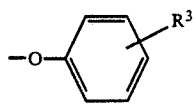

where R³ is alkylsulfonamido of 1 to 6 carbon atoms, arylsulfonamido of 6 to 10 carbon atoms, —NO₂, —CN, 1-imidazolyl or 1,2,4-triazol-1-yl;

or a pharmaceutically acceptable salt thereof.

2. A compound of claim 1 of the formula:

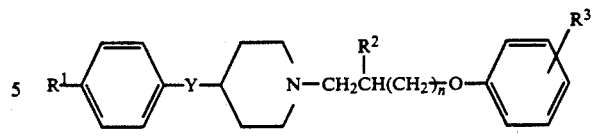

in which

R¹ is alkylsulfonamido of 1 to 3 carbon atoms;

Y is

or —O—;

R² is —H or —OH;

n is 0 or 1 and when R² is —OH, n is 1;

R³ is —NO₂, alkylsulfonamido of 1 to 3 carbon atoms, or 1-imidazolyl or a pharmaceutically acceptable salt thereof.

3. A compound of claim 1, which is N-[4-[[1-[2-(4-nitrophenoxy)ethyl]-4-piperidinyl]carbonyl]phenyl]methanesulfonamide, or a pharmaceutically acceptable salt thereof.

4. A compound of claim 1 which is N-[4-[2-[4-4-[(methylsulfonyl)amino]benzoyl]-1-piperidinyl]ethoxy]phenyl]methanesulfonamide, or a pharmaceutically acceptable salt thereof.

5. A compound of claim 1 which is N-[4-[[1-[3-(4-nitrophenoxy)propyl]-4-piperidinyl]carbonyl]phenyl]methanesulfonamide, or a pharmaceutically acceptable salt thereof.

6. A compound of claim 1 which is N-[4-[[1-[2-[4-(methylsulfonyl)amino]phenoxy]ethyl-4-piperidinyl]oxy]phenyl]methanesulfonamide, or a pharmaceutically acceptable salt thereof.

7. A compound of claim 1 which is N-[4-[[1-[3-[4-(1H-imidazol-1-yl)phenyl]propyl]-4-piperidinyl]carbonyl]phenyl]methanesulfonamide dihydrochloride, or a pharmaceutically acceptable salt thereof.

8. A compound of claim 1 which is N-[4-[2-hydroxy-3-[4-[4-[(methylsulfonyl)amino]benzoyl]-1-piperidinyl]propoxyl]phenyl]methanesulfonamide, or a pharmaceutically acceptable salt thereof.

* * * * *